(12) United States Patent
Shah et al.

(10) Patent No.: US 10,758,219 B2
(45) Date of Patent: Sep. 1, 2020

(54) LAPAROSCOPIC TISSUE MANIPULATION DEVICE

(71) Applicant: Covidien LP, Mansfield, MA (US)

(72) Inventors: Monali Naimish Shah, Milton, GA (US); Aken Jatin Sanghavi, Mumbai (IN); Asahi Murata, Atlanta, GA (US); Shyam Jay Nathu, Johns Creek, GA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/185,043

(22) Filed: Nov. 9, 2018

(65) Prior Publication Data
US 2019/0183478 A1   Jun. 20, 2019

Related U.S. Application Data

(60) Provisional application No. 62/598,537, filed on Dec. 14, 2017.

(51) Int. Cl.
*A61B 17/02* (2006.01)
*A61B 17/29* (2006.01)
(Continued)

(52) U.S. Cl.
CPC .......... *A61B 17/0218* (2013.01); *A61B 17/29* (2013.01); *A61B 1/32* (2013.01);
(Continued)

(58) Field of Classification Search
CPC .................... A61B 1/32; A61B 1/3132; A61B 17/02–0206; A61B 17/0218; A61B 17/0281; A61B 2017/0212
See application file for complete search history.

(56) References Cited

U.S. PATENT DOCUMENTS

| 1,947,649 A | * | 2/1934 | Kadavy | .............. | A61B 17/0293 |
| | | | | | 600/203 |
| 2,202,748 A | * | 5/1940 | Solo | ....................... | A61B 17/24 |
| | | | | | 606/204.45 |

(Continued)

FOREIGN PATENT DOCUMENTS

EP          0449663 A2    10/1991

OTHER PUBLICATIONS

European Search Report dated Apr. 4, 2019, issued in EP Appln. No. 18212212.

*Primary Examiner* — Jacqueline T Johanas
*Assistant Examiner* — Michelle C Eckman
(74) *Attorney, Agent, or Firm* — Carter, DeLuca & Farrell LLP (57) ABSTRACT

A laparoscopic tissue manipulator device includes a handle assembly, an elongate body, and a tool assembly. The tool assembly is supported on the distal portion of the elongate body and includes fingers. Each of the fingers includes a body having an elongate U-shaped configuration with a blunt distal end and an open interior and is secured to a distal portion of the elongate body about a first pivot member. The fingers are pivotable from a contracted position in which the fingers are aligned with each other and with the second longitudinal axis and an expanded position in which the fingers are splayed outwardly from the first pivot member at different angular positions in relation to the second longitudinal axis. A cover is supported on the each of the fingers to cover the open interior of the body of the fingers.

19 Claims, 4 Drawing Sheets

(51) Int. Cl.
    *A61B 1/32*      (2006.01)
    *A61B 17/00*     (2006.01)
    *A61B 17/30*     (2006.01)
(52) U.S. Cl.
    CPC .............. *A61B 2017/00907* (2013.01); *A61B 2017/2927* (2013.01); *A61B 2017/301* (2013.01)

(56) References Cited

U.S. PATENT DOCUMENTS

| | | | | |
|---|---|---|---|---|
| 3,667,474 | A * | 6/1972 | Lapkin | A61M 29/02 606/198 |
| 4,190,042 | A * | 2/1980 | Sinnreich | A61B 1/32 600/204 |
| 5,007,409 | A * | 4/1991 | Pope | A61B 1/00142 600/203 |
| 5,080,088 | A * | 1/1992 | LeVahn | A61B 17/02 600/206 |
| 5,113,846 | A * | 5/1992 | Hiltebrandt | A61B 1/32 600/225 |
| 5,178,133 | A * | 1/1993 | Pena | A61B 1/00142 600/203 |
| 5,195,505 | A * | 3/1993 | Josefsen | A61B 17/0218 600/204 |
| 5,195,506 | A * | 3/1993 | Hulfish | A61B 17/0218 600/204 |
| 5,199,419 | A * | 4/1993 | Remiszewski | A61B 1/32 600/204 |
| 5,235,966 | A * | 8/1993 | Jamner | A61B 17/0218 600/204 |
| 5,245,987 | A * | 9/1993 | Redmond | A61B 17/0218 600/204 |
| 5,271,385 | A | 12/1993 | Bailey | |
| 5,289,817 | A * | 3/1994 | Williams | A61B 17/0218 294/97 |
| 5,307,805 | A * | 5/1994 | Byrne | A61B 17/0218 600/214 |
| 5,339,801 | A * | 8/1994 | Poloyko | A61B 17/0218 600/214 |
| 5,339,803 | A * | 8/1994 | Mayzels | A61B 17/0218 600/201 |
| 5,351,679 | A * | 10/1994 | Mayzels | A61B 17/0218 600/214 |
| 5,353,784 | A * | 10/1994 | Nady-Mohamed | A61B 17/0218 600/205 |
| 5,358,496 | A * | 10/1994 | Ortiz | A61B 17/0218 604/104 |
| 5,381,788 | A | 1/1995 | Matula et al. | |
| 5,383,888 | A * | 1/1995 | Zvenyatsky | A61B 17/0218 600/564 |
| 5,390,664 | A * | 2/1995 | Redmond | A61B 17/0218 600/224 |
| 5,391,180 | A * | 2/1995 | Tovey | A61B 1/32 600/224 |
| 5,441,044 | A * | 8/1995 | Tovey | A61B 17/0218 600/215 |
| 5,456,695 | A * | 10/1995 | Herve Dallemagne | A61B 17/0218 606/198 |
| 5,490,819 | A * | 2/1996 | Nicholas | A61B 1/32 600/201 |
| 5,514,157 | A * | 5/1996 | Nicholas | A61B 17/0218 600/201 |
| 5,549,636 | A * | 8/1996 | Li | A61B 17/0218 606/205 |
| 5,554,101 | A | 9/1996 | Matula et al. | |
| 5,613,950 | A * | 3/1997 | Yoon | A61B 17/00234 600/225 |
| 5,656,012 | A * | 8/1997 | Sienkiewicz | A61B 17/0218 600/201 |
| 5,662,676 | A * | 9/1997 | Koninckx | A61B 17/0218 600/210 |
| 5,722,935 | A * | 3/1998 | Christian | A61B 17/0281 600/204 |
| 5,755,661 | A * | 5/1998 | Schwartzman | A61B 17/02 600/204 |
| 5,800,394 | A * | 9/1998 | Yoon | A61B 17/00234 600/207 |
| 5,803,902 | A * | 9/1998 | Sienkiewicz | A61B 17/0218 128/853 |
| 5,891,162 | A * | 4/1999 | Sugarbaker | A61B 17/29 606/151 |
| 5,904,649 | A * | 5/1999 | Andrese | A61B 17/0218 600/204 |
| D411,883 | S * | 7/1999 | Farascioni | D24/135 |
| 6,036,638 | A * | 3/2000 | Nwawka | A61B 1/00142 600/186 |
| 6,221,008 | B1 * | 4/2001 | Keckstein | A61B 17/0281 600/204 |
| 6,432,048 | B1 * | 8/2002 | Francois | A61B 1/303 600/186 |
| 6,494,211 | B1 * | 12/2002 | Boyd | A61B 17/00234 128/898 |
| 8,092,378 | B2 * | 1/2012 | Roth | A61B 17/072 600/206 |
| 8,313,507 | B2 * | 11/2012 | Ravikumar | A61B 17/0218 606/205 |
| 8,906,045 | B2 * | 12/2014 | Levin | A61B 17/00491 606/151 |
| 9,011,318 | B2 * | 4/2015 | Choset | A61B 1/00006 600/114 |
| 9,095,348 | B2 * | 8/2015 | Truckai | A61B 18/1485 |
| 9,113,939 | B2 * | 8/2015 | Strokosz | A61B 17/2909 |
| 9,119,654 | B2 * | 9/2015 | Ramans | A61B 34/71 |
| 9,333,001 | B2 * | 5/2016 | Stokes | A61B 17/29 |
| 9,468,426 | B2 * | 10/2016 | Conlon | A61B 17/29 |
| 9,545,283 | B2 * | 1/2017 | Sack | A61B 17/1671 |
| 9,999,470 | B1 * | 6/2018 | Passons | A61B 34/30 |
| 10,327,749 | B1 * | 6/2019 | Passons | A61B 17/0218 |
| 2002/0077532 | A1 * | 6/2002 | Gannoe | A61B 17/02 600/232 |
| 2002/0115909 | A1 * | 8/2002 | Bolser | A61B 17/00008 600/210 |
| 2003/0220650 | A1 * | 11/2003 | Major | A61B 17/025 606/90 |
| 2005/0080425 | A1 * | 4/2005 | Bhatnagar | A61B 17/02 606/90 |
| 2005/0192482 | A1 * | 9/2005 | Carpenter | A61B 1/00142 600/203 |
| 2005/0228232 | A1 * | 10/2005 | Gillinov | A61B 17/02 600/209 |
| 2005/0240083 | A1 * | 10/2005 | Orban, III | A61B 17/0218 600/210 |
| 2005/0251196 | A1 * | 11/2005 | Wong | A61B 17/3439 606/198 |
| 2006/0052670 | A1 * | 3/2006 | Stearns | A61B 1/0056 600/216 |
| 2006/0052671 | A1 * | 3/2006 | McCarthy | A61B 17/0206 600/232 |
| 2006/0094932 | A1 * | 5/2006 | Goldfarb | A61B 17/02 600/229 |
| 2006/0259020 | A1 * | 11/2006 | Sharratt | A01N 25/34 606/1 |
| 2007/0060939 | A1 * | 3/2007 | Lancial | A61B 1/00154 606/191 |
| 2007/0270656 | A1 * | 11/2007 | Bayat | A61B 17/02 600/214 |
| 2008/0039256 | A1 * | 2/2008 | Jinno | A61B 34/70 474/148 |
| 2008/0058833 | A1 * | 3/2008 | Rizvi | A61B 17/4241 606/119 |
| 2008/0108877 | A1 * | 5/2008 | Bayat | A61B 17/02 600/214 |
| 2008/0114210 | A1 * | 5/2008 | Shah | A61B 1/00135 600/220 |

(56) References Cited

U.S. PATENT DOCUMENTS

| | | | |
|---|---|---|---|
| 2008/0242938 A1* | 10/2008 | Larkin | A61B 1/00142 600/203 |
| 2009/0149716 A1* | 6/2009 | Diao | A61B 1/00085 600/202 |
| 2010/0106052 A1* | 4/2010 | Uznanski | A61B 10/04 600/562 |
| 2011/0040152 A1* | 2/2011 | Kim | A61B 17/0218 600/206 |
| 2011/0105848 A1* | 5/2011 | Sadovsky | A61B 17/0218 600/204 |
| 2011/0144450 A1* | 6/2011 | Paolitto | A61B 17/0206 600/224 |
| 2011/0301424 A1* | 12/2011 | Steigerwald | A61B 1/303 600/235 |
| 2012/0088978 A1* | 4/2012 | Park | A61B 17/00234 600/204 |
| 2012/0130181 A1* | 5/2012 | Davis | A61B 17/3423 600/206 |
| 2013/0066136 A1* | 3/2013 | Palese | A61B 17/52 600/11 |
| 2014/0052143 A1* | 2/2014 | Deitch | A61B 17/42 606/119 |
| 2015/0065805 A1* | 3/2015 | Edmondson | A61B 17/0218 600/204 |
| 2017/0095241 A1* | 4/2017 | Perler | A61B 90/30 |
| 2018/0042595 A1* | 2/2018 | Tsubouchi | A61B 17/0206 |
| 2018/0280013 A1* | 10/2018 | Ravikumar | A61B 17/0218 |
| 2019/0274728 A1* | 9/2019 | LaPierre | A61B 17/7074 |

* cited by examiner

LAPAROSCOPIC TISSUE MANIPULATION DEVICE

CROSS-REFERENCE TO RELATED APPLICATION

This application claims the benefit of and priority to U.S. Provisional Patent Application No. 62/598,537 filed Dec. 14, 2017, the entire disclosure of which is incorporated by reference herein.

BACKGROUND

1. Technical Description

The present disclosure is directed to a tissue manipulation device and, more particularly, to a tissue manipulation device configured to improve visualization of and access to a surgical site during a laparoscopic surgical procedure.

2. Background of Related Art

Surgical tissue manipulation devices, e.g., surgical retractors, suitable for use during laparoscopic surgical procedures are well known. During certain laparoscopic procedures such as liver resections, existing manipulation devices provide limited access to a surgical site and limited visibility of tissue being treated as well as adjacent tissues. In addition, existing manipulation devices scoop and elevate tissue but do not have a gripping capability. This makes movement of the tissue in a controlled manner difficult for a surgeon.

A continuing need exists in the surgical arts for a tissue manipulation device that is suitable for laparoscopic use, provides improved visibility and accessibility to a surgical site, and has a gripping capability.

SUMMARY

One aspect of the present disclosure is directed to a laparoscopic tissue manipulator device including a handle assembly, an elongate body extending distally from the handle assembly, and a tool assembly. The elongate body includes a proximal portion defining a first longitudinal axis and a distal portion defining a second longitudinal axis. The tool assembly is supported on the distal portion of the elongate body and includes a plurality of fingers. Each of fingers includes a body having an elongate U-shaped configuration with a blunt distal end and an open interior. Each of the fingers is secured to the distal portion of the elongate body about a first pivot member. The fingers are pivotable about an axis defined by the first pivot member from a contracted position in which the fingers are aligned with each other and with the second longitudinal axis and an expanded position in which the fingers are splayed outwardly from the first pivot member at different angular positions in relation to the second longitudinal axis. A cover is supported on the each of the fingers to cover the open interior of the body of the fingers.

In embodiments, the cover is formed from a hydrophilic material.

In some embodiments, the cover is formed from a porous textile material.

In certain embodiments, the cover is formed of a transparent material.

In embodiments, each of the plurality of fingers includes a proximal portion and a distal portion. The distal portion of the body is secured to the proximal portion of the body by a second pivot member such that the distal portion of the body can be pivoted in relation to the proximal portion of the body.

In some embodiments, the proximal portion of the body of each of fingers defines a plane and the second pivot member extends in a direction parallel to the plane.

In certain embodiments, a distal end of the proximal portion of the body of each of the fingers and a proximal end of the distal portion of the body of each of the fingers are configured to interact to limit pivotable movement of the distal portion of the body in relation to the proximal portion of the body to 45 degrees.

In embodiments, the distal portion of the elongate body is secured to the proximal portion of the elongate body by a third pivot member such that the distal portion of the elongate body is pivotable in relation to the proximal portion of the elongate body about an axis defined by the third pivot member.

In some embodiments, the handle assembly includes an actuator that is operably connected to the tool assembly and is movable to move the plurality of fingers between the contracted position and the expanded position.

In certain embodiments, the handle assembly includes an actuator that is operably connected to the distal portion of the body of each of the fingers and is movable to pivot the distal portion of each of the fingers in relation to a respective proximal portion of the body of each of fingers.

In embodiments, the handle assembly includes an actuator that is operably connected to the distal portion of the elongate body and the actuator is movable to pivot the distal portion of the elongate body in relation to the proximal portion of the elongate body.

BRIEF DESCRIPTION OF THE DRAWINGS

Various embodiments of the presently disclosed laparoscopic tissue manipulation device are described herein below with reference to the drawings, wherein.

DETAILED DESCRIPTION OF EMBODIMENTS

Embodiments of the presently disclosed tissue manipulation device will now be described in detail with reference to the drawings in which like reference numerals designate identical or corresponding elements in each of the several views. It is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "laparoscopic" is used generally used to refer to endoscopic, arthroscopic, and/or any other procedure conducted through small diameter incision or cannula. In addition, the term "clinician" is used generally to refer to medical personnel including doctors, nurses, and support personnel.

Figure 1:
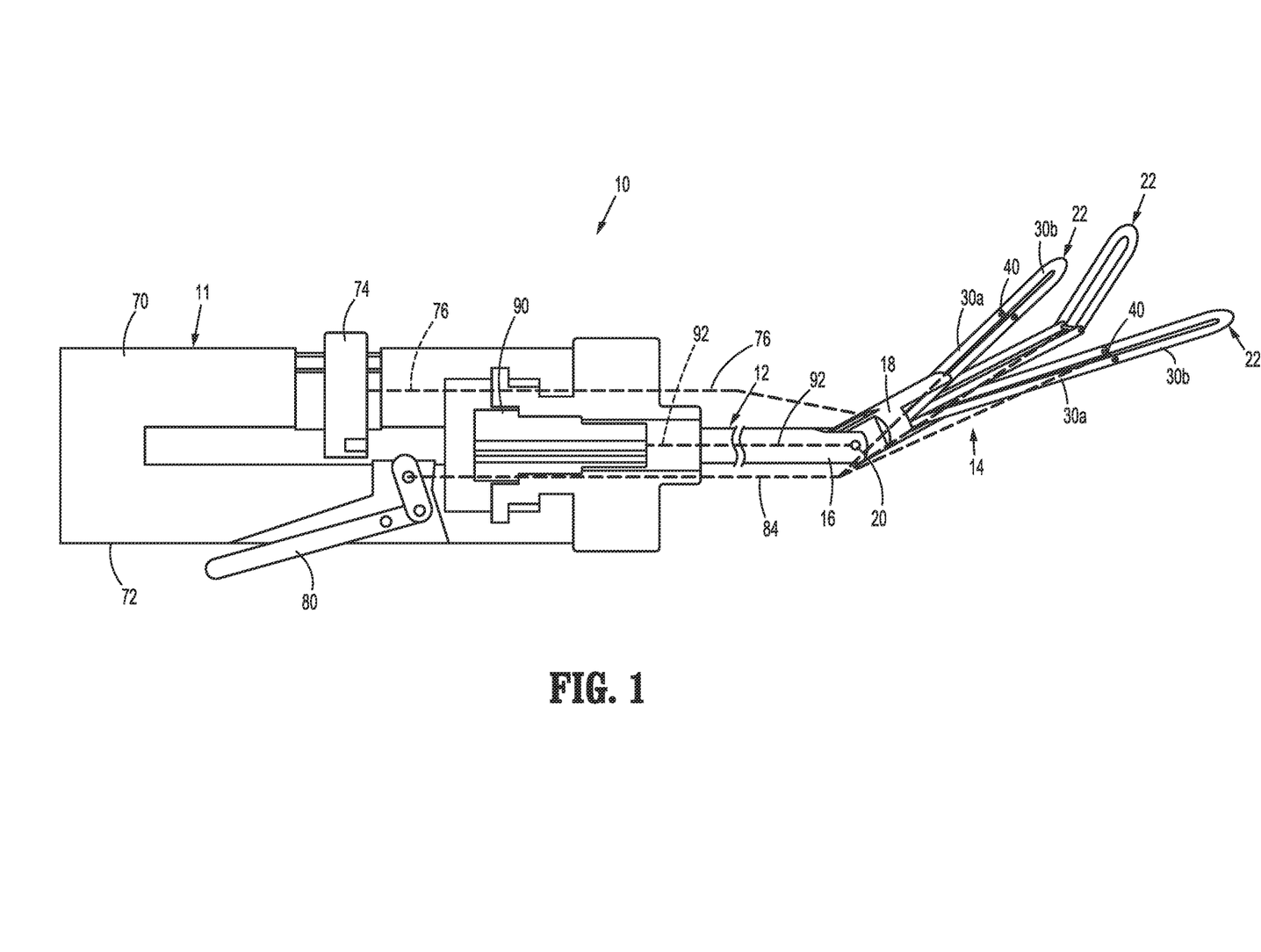
FIG. 1 is a schematic view of an exemplary embodiment of the presently disclosed tissue manipulation device with a tool assembly shown in an expanded position.

An exemplary embodiment of the presently disclosed tissue manipulation device 10 includes a handle assembly 11, an elongate body 12, and a tool assembly 14. In embodiments, the elongate body 12 includes a proximal portion 16 and a distal portion 18. The distal portion 18 of the elongate body 12 is secured to the proximal portion 16 of the elongate body 12 by a pivot member 20. The tool assembly 14 is supported on the distal portion 18 of the elongate body 12 such that the distal portion 18 of the elongate body 12 and the tool assembly 14 can articulate about the pivot member 20 in relation to the proximal portion 16 of the elongate body 12.

Figure 2:
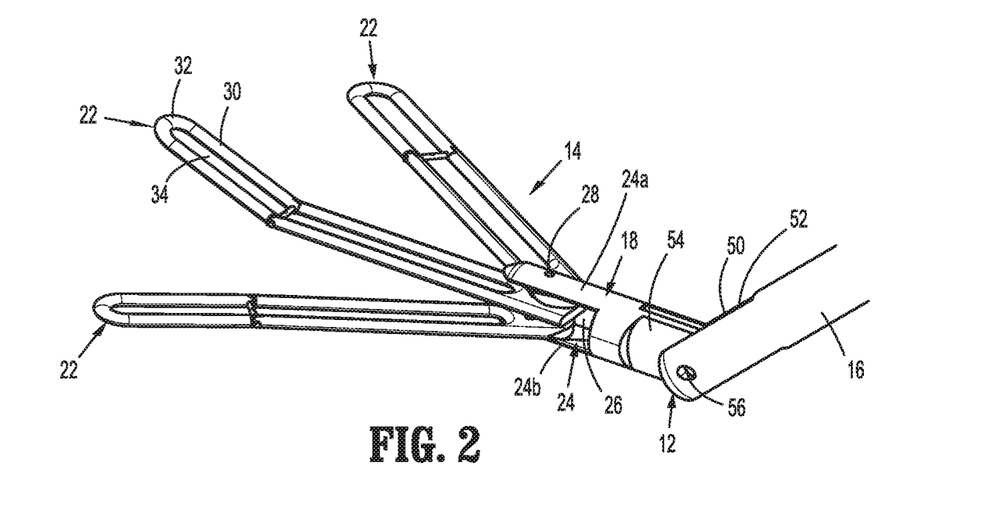
FIG. 2 is a side perspective view of a distal portion of the device shown in FIG. 1.
Figure 3:
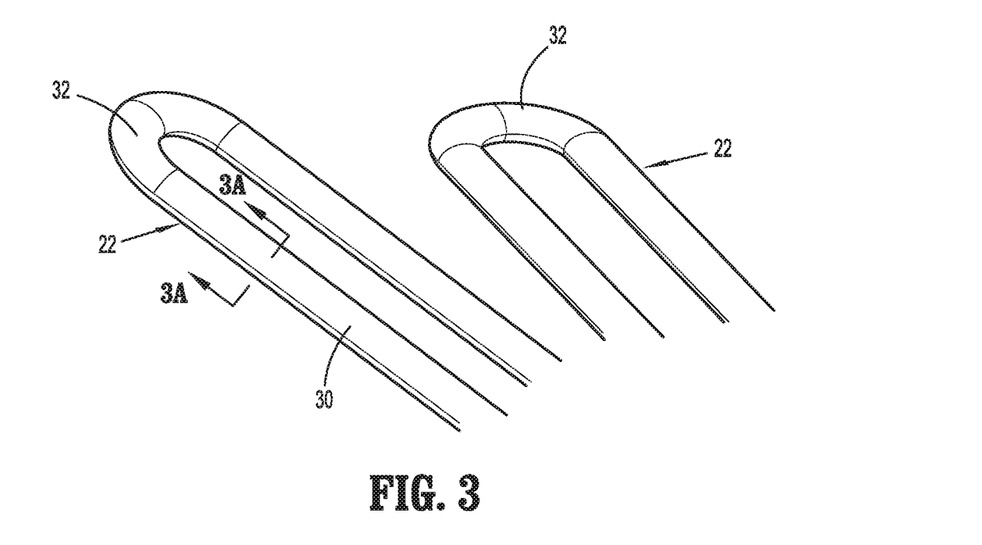
FIG. 3 is a side perspective view of a distal portion of fingers of the tool assembly shown in FIG. 2.
Figure 4:
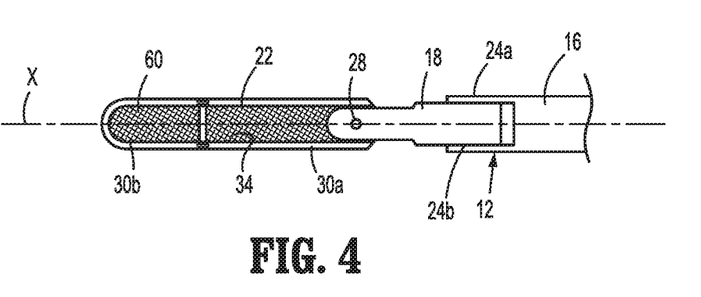
FIG. 4 is a top view of the distal end of the device shown in FIG. 1 with the tool assembly in a contracted position.
Figure 4A:
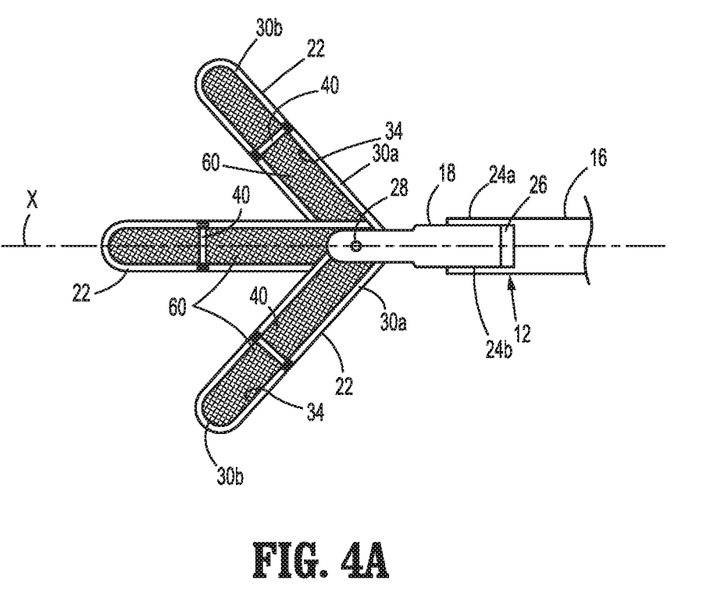
FIG. 4A is a top view of the distal end of the device shown in FIG. 1 with the tool assembly in the expanded position.

Referring to FIGS. 2-4, in embodiments, the tool assembly 14 includes a plurality of fingers 22 and the distal portion 18 of the elongate body 12 defines a yoke 24. The yoke 24 includes a first extension 24a and a second extension 24b that are spaced from each other and define a recess 26. The fingers 22 have a proximal end that is received within the recess 26 and a distal end that projects distally from the yoke 24 of distal portion 18 of the elongate body 12. The fingers 22 are pivotable about a pivot member 28, which is fixedly positioned between the first extension 24a and the second extension 24b of the yoke 24, between a contracted position in which the fingers 22 are aligned with each other along a longitudinal axis "X" (FIG. 4) defined by the distal portion 18 of the elongate body 12 and an expanded position in which the fingers 22 are splayed outwardly of each other at different angular positions to define a fan configuration (FIG. 4A)

Figure 5:
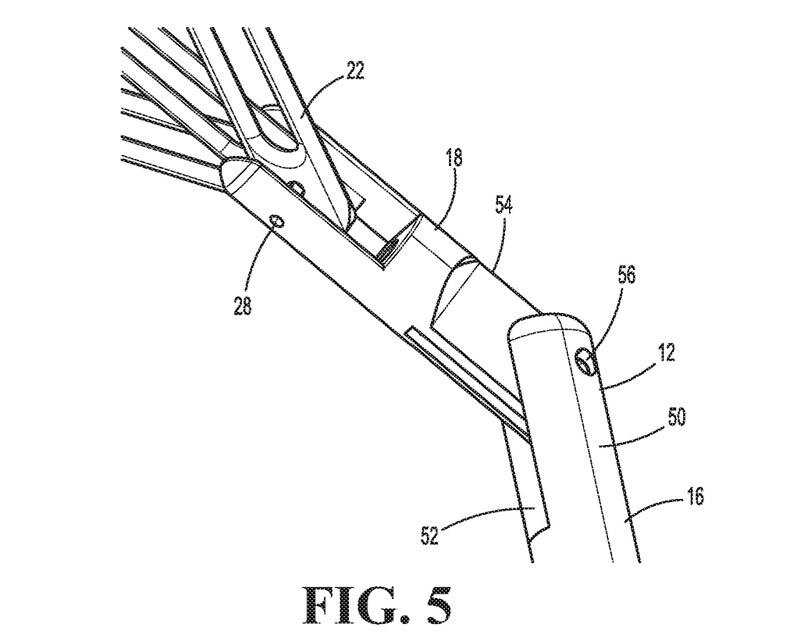
FIG. 5 is a side perspective view of a central portion of the device shown in FIG. 1.

Referring also to FIG. 5, in embodiments, the proximal end of each on the fingers 22 defines a cam slot (not shown) that receives the pivot member 28. The cam slots of the fingers 22 are configured such that axial movement of the fingers 22 in relation to the pivot member 28 between retracted and advanced positions causes the fingers 22 to move between the contracted position and the expanded position. U.S. Pat. Nos. 5,391,180 and 5,554,101 disclose tool assemblies that are actuated in a similar manner and are incorporated herein in their entirety by reference. Alternately, other known actuation mechanisms can be used to move the fingers 22 between aligned and splayed configurations.

The tool assembly has a diameter that is minimized in the contracted position of the fingers 22. As such, the tool assembly 14 can be advanced through a small diameter trocar (not shown), e.g., a 5 mm, 10 mm, or 15 mm trocar, when the fingers 22 are in the contracted position.

Figure 3A:
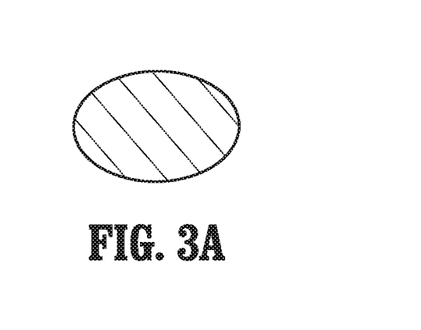
FIG. 3A is a cross-sectional view taken along section line 3A-3A of FIG. 3.

Referring to FIGS. 2 and 3, each of the fingers 22 includes a body 30 having an elongated U-shape with a rounded, blunt distal end 32 and an open interior 34. In embodiments, the body 30 is formed from a substantially rigid, biocompatible material, such as a metal, polymeric material, or combination thereof. The body 30 can have a circular or oval cross-sectional shape (FIG. 3A) that has a smooth external surface to reduce the likelihood of the fingers 22 snagging or damaging tissue during advancement of the tool assembly 14 to a surgical site and during manipulation of tissue with the tool assembly 14.

Figure 6:
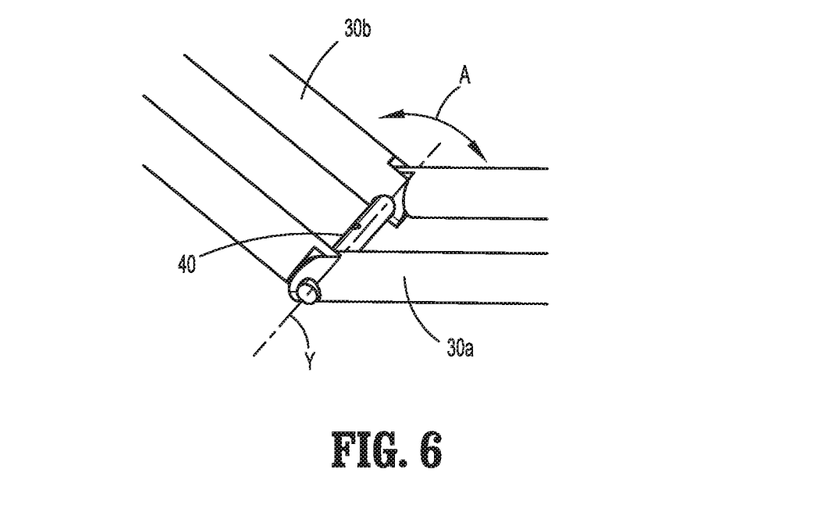
FIG. 6 is a side perspective view of a central portion of one of the fingers of the tool assembly shown in FIG. 2.

Referring also to FIG. 6, the body 30 of each of the fingers 22 includes a proximal portion 30a and a distal portion 30b. The distal portion 30b of the body 30 is coupled to the proximal portion 30a by a pivot member 40 such that the distal portion 30b of the body 30 can be pivoted in relation to the proximal portion 30a in the directions indicated by arrow "A" in FIG. 6. The pivot member 40 defines an axis "Y" (FIG. 6) that extends in a direction parallel to a plane defined by the proximal portion 30a of the body 30. This allows the distal portion 30b to pivot about the pivot member 40 into and out of the plane defined by the proximal portion 30a.

In embodiments, the distal end of the proximal portion 30a of the body 30 of the fingers 22 and the proximal end of the distal portion 30b of the body 30 of the fingers 22 are configured to interact to limit pivotable movement of the distal portion 30b in relation to the proximal portion 30a to about 45 degrees. Alternately, other degrees of pivotable movement are envisioned.

In embodiments, the tool assembly 14 includes three fingers 22. However, it is envisioned that the tool assembly 14 may include 2 or more fingers 22. For example, the tool assembly 14 may include 4 or 5 fingers 22.

Referring again to FIGS. 2 and 5, the proximal portion 16 of the elongate body 12 includes a yoke 50 that defines a recess 52. The distal portion 18 of the elongate body 12 includes a proximally extending bracket 54. The proximally extending bracket 54 of the distal portion 18 of the elongate body 12 is secured within the recess 52 by a pivot member 56 such that the distal portion 18 of the elongate body 12 is pivotable in relation to the proximal portion 16. In embodiments, the longitudinal axis of the pivot member 56 is substantially parallel to the longitudinal axis of the pivot member 40 of the fingers 12. In this embodiment, when the distal portion 18 of the elongate body 12 is pivoted in relation to the proximal portion 16 of the elongate body 12, the plane defined by the proximal portion 30a of the body 30 of the fingers 22 is rotated about the longitudinal axis of the pivot member 56.

Referring to FIG. 4, in embodiments, the open interior 34 of the body 30 of each of the fingers 22 is covered with a material 60. In embodiments, the material 60 can be a textile material such as a hernia mesh material. In some embodiments, the material 60 is macro porous and hydrophilic. In some embodiments, the material 60 is substantially non-opaque or transparent. A macro porous and hydrophilic material allows for tissue to be more easily gripped by the fingers 22. In addition, by providing a transparent covering, visualization of the surgical site is improved.

Referring again to FIG. 1, the handle assembly 11 includes a body 70 defining a grip 72. The body 70 of the handle assembly 11 includes a first actuator 74 that is operably coupled to the fingers 22 by a linkage shown schematically as 76 such that the first actuator 74 is movable to move the fingers 22 from the contracted position (FIG. 4) to the expanded position (FIG. 4A). In embodiments, the first actuator 74 is a switch that is slidable on the body 70 of the handle assembly 11.

The body 70 also supports a second actuator 80 that is operably coupled to the distal portion 30b of the body 30 of the fingers 22 by a linkage shown schematically as 84. The second actuator 80 is movable on the body 70 of the handle assembly 11 to pivot the distal portion 30b of each of a respective finger 30 about the pivot member 40. In embodiments, the second actuator 80 includes a pivotable lever. Alternately, other types of actuator mechanisms can be used to pivot the distal portion 30b of a finger 22 in relation to a proximal portion 30a of the respective finger 22. It is noted that a single actuator 80 can be used to pivot all of the distal portions 30b of the fingers 22 simultaneously or separate actuators can be provided to independently control pivotable movement of each of the fingers 22.

The handle assembly 11 also includes a third actuator 90 that is coupled to the distal portion 18 of the elongate body 12 by a linkage shown schematically as 92. The third actuator 90 is movable on the body 70 of the handle assembly 11 to pivot the distal portion 18 of the elongate body 12 about the pivot member 56 in relation to the proximal portion 16 of the elongate body 12.

The presently disclosed laparoscopic tissue manipulation device 10 is suitable for use in the performance of a variety of laparoscopic procedures. The laparoscopic tissue manipulation device 10 is particularly suited for use in liver resection procedures. Due to the configuration of the fingers 22, the device 10 is less likely to damage the liver because the device 10 applies less compression to the liver parenchyma. The configuration of the fingers 22 of the device 10 also allows the liver to be gripped to provide a surgeon with better control to minimize trauma to the liver and to adjacent tissues.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A laparoscopic tissue manipulator device comprising:
    a handle assembly;
    an elongate body extending distally from the handle assembly, the elongate body including a proximal portion defining a first longitudinal axis and a distal portion defining a second longitudinal axis;
    a tool assembly supported on the distal portion of the elongate body, the tool assembly including a plurality of fingers, each of the plurality of fingers including a body having an elongate U-shaped configuration with a blunt distal end and an open interior, each of the plurality of fingers being secured to the distal portion of the elongate body about a first pivot member, the plurality of fingers being pivotable about an axis defined by the first pivot member from a contracted position in which the plurality of fingers are aligned with each other and with the second longitudinal axis and an expanded position in which the plurality of fingers are splayed outwardly from the first pivot member at different angular positions in relation to the second longitudinal axis; and
    a cover supported on the each of the plurality of fingers, each of the covers supported on a respective finger of the plurality of fingers to cover the open interior of the body of the respective finger.

2. The laparoscopic tissue manipulator device of claim 1, wherein the cover is formed from a hydrophilic material.

3. The laparoscopic tissue manipulator device of claim 2, wherein the cover is formed from a porous textile material.

4. The laparoscopic tissue manipulator device of claim 2, wherein the cover is formed of a transparent material.

5. The laparoscopic tissue manipulator device of claim 1, wherein each of the plurality of fingers includes a proximal portion and a distal portion, the distal portion of the body of each of the plurality of fingers being secured to a respective proximal portion of the body of one of the plurality of fingers by a second pivot member such that the distal portion of the body of each of the plurality of fingers of the body can be pivoted in relation to the proximal portion of the body of the plurality of fingers.

6. The laparoscopic tissue manipulator device of claim 5, wherein the proximal portion of the body of each of the plurality of fingers defines a plane, and the second pivot member extends in a direction parallel to the plane.

7. The laparoscopic tissue manipulator device of claim 6, wherein a distal end of the proximal portion of the body of each of the plurality of fingers and a proximal end of the distal portion of the body of each of the plurality of fingers are configured to interact to limit pivotable movement of the distal portion in relation to the proximal portion to 45 degrees.

8. The laparoscopic tissue manipulator device of claim 5, wherein the handle assembly includes an actuator that is operably connected to the distal portion of the body of each of the plurality of fingers and is movable to pivot the distal portion of each of the plurality of fingers in relation to a respective proximal portion of the body of each of the plurality of fingers.

9. The laparoscopic tissue manipulator device of claim 1, wherein the handle assembly includes an actuator that is operably connected to the tool assembly and is movable to move the plurality of fingers between the contracted position and the expanded position.

10. A laparoscopic tissue manipulator device comprising:
    a handle assembly;
    an elongate body extending distally from the handle assembly, the elongate body including a proximal portion defining a first longitudinal axis and a distal portion defining a second longitudinal axis;
    a tool assembly supported on the distal portion of the elongate body, the tool assembly including a plurality of fingers, each of the plurality of fingers including a body having an elongate U-shaped configuration with a blunt distal end and an open interior, each of the plurality of fingers being secured to the distal portion of the elongate body about a first pivot member, the plurality of fingers being pivotable about an axis defined by the first pivot member from a contracted position in which the plurality of fingers are aligned with each other and with the second longitudinal axis and an expanded position in which the plurality of fingers are splayed outwardly from the first pivot member at different angular positions in relation to the second longitudinal axis; and
    a cover supported on the each of the plurality of fingers to cover the open interior of the body of the respective finger;
    wherein the distal portion of the elongate body is secured to the proximal portion of the elongate body by a third pivot member, the distal portion of the elongate body being pivotable in relation to the proximal portion of the elongate body about an axis defined by the third pivot member.

11. The laparoscopic tissue manipulator device of claim 10, wherein the handle assembly includes an actuator that is operably connected to the distal portion of the elongate body, the actuator being movable to pivot the distal portion of the elongate body in relation to the proximal portion of the elongate body.

12. A laparoscopic tissue manipulator device comprising:
a handle assembly;
an elongate body extending distally from the handle assembly, the elongate body including a proximal portion defining a first longitudinal axis and a distal portion defining a second longitudinal axis;
a tool assembly supported on the distal portion of the elongate body, the tool assembly including a plurality of fingers, each of the plurality of fingers being secured to the distal portion of the elongate body about a first pivot member and including a body having an elongate U-shaped configuration with a blunt distal end and an open interior, the plurality of fingers being pivotable about an axis defined by the first pivot member from a contracted position in which the plurality of fingers are aligned with each other and with the second longitudinal axis and an expanded position in which the plurality of fingers are splayed outwardly from the first pivot member at different angular positions in relation to the second longitudinal axis, wherein the distal portion of the elongate body is secured to the proximal portion of the elongate body by a third pivot member, the distal portion of the elongate body being pivotable in relation to the proximal portion of the elongate body about an axis defined by the third pivot member.

13. The laparoscopic tissue manipulator device of claim 12, further including a cover supported on the each of the plurality of fingers, each of the covers supported on a respective finger of the plurality of fingers to cover the open interior of the body of the respective finger.

14. The laparoscopic tissue manipulator device of claim 13, wherein the cover is formed from a hydrophilic material.

15. The laparoscopic tissue manipulator device of claim 13, wherein the cover is formed from a porous textile material.

16. The laparoscopic tissue manipulator device of claim 13, wherein the cover is formed of a transparent material.

17. The laparoscopic tissue manipulator device of claim 13, wherein each of the plurality of fingers includes a proximal portion and a distal portion, the distal portion of the body of each of the plurality of fingers being secured to a respective proximal portion of the body of one of the plurality of fingers by a second pivot member such that the distal portion of the body of each of the plurality of fingers of the body can be pivoted in relation to the proximal portion of the body of the plurality of fingers.

18. The laparoscopic tissue manipulator device of claim 17, wherein the proximal portion of the body of each of the plurality of fingers defines a plane, and the second pivot member extends in a direction parallel to the plane.

19. The laparoscopic tissue manipulator device of claim 18, wherein a distal end of the proximal portion of the body of each of the plurality of fingers and a proximal end of the distal portion of the body of each of the plurality of fingers are configured to interact to limit pivotable movement of the distal portion in relation to the proximal portion to 45 degrees.

* * * * *